United States Patent [19]
Uehara et al.

[11] Patent Number: 5,947,923
[45] Date of Patent: Sep. 7, 1999

[54] BREAST PUMP

[75] Inventors: Hiroyuki Uehara; Yoichi Nakata, both of Tokyo, Japan

[73] Assignee: Pigeon Corporation, Tokyo, Japan

[21] Appl. No.: 08/809,595

[22] PCT Filed: Jul. 25, 1996

[86] PCT No.: PCT/JP96/02092

§ 371 Date: May 23, 1997

§ 102(e) Date: May 23, 1997

[87] PCT Pub. No.: WO97/04822

PCT Pub. Date: Feb. 13, 1997

[30] Foreign Application Priority Data

Jul. 31, 1995 [JP] Japan ................................. 7-214040

[51] Int. Cl.⁶ .................................................. A61M 1/06
[52] U.S. Cl. ............................ 604/74; 604/74; 604/346; 417/306
[58] Field of Search ............................. 604/73, 74, 327, 604/346, 355, 902, 118, 119, 133, 149, 151, 152; 417/306, 440

[56] References Cited

U.S. PATENT DOCUMENTS

| 4,673,388 | 6/1987 | Schlensog et al. | 604/74 |
| 4,759,747 | 7/1988 | Aida et al. | 604/74 |
| 4,883,464 | 11/1989 | Morifuji | 604/74 |
| 4,886,494 | 12/1989 | Morifuji | 604/74 |
| 4,892,517 | 1/1990 | Yuan et al. | 604/74 |
| 4,964,851 | 10/1990 | Larsson | 604/74 |

FOREIGN PATENT DOCUMENTS 198-469  10/1986  European Pat. Off. ................. 604/73

Primary Examiner—Wynn Wood Coggins
Assistant Examiner—LoAn H. Thanh
Attorney, Agent, or Firm—Armstrong, Westerman, Hattori, McLeland & Naughton

[57] ABSTRACT

A breast pump for sucking out mother's milk is provided, the breast pump including a sucking portion 11, 12, 13 to be fitted to one's breast, a negative pressure generating member 14 mounted in the sucking portion for generating negative pressures therein, a driving member 24 attached to the sucking portion, a driving power transmitting member 25 attached to the sucking portion for repeatedly generating negative pressures by transmitting a driving power of the driving member, and a reservoir 30 connected to the sucking portion for reserving mother's milk from the sucking portion.

8 Claims, 14 Drawing Sheets

BREAST PUMP

FIELD OF THE INVENTION

This invention relates to a breast pump for sucking out mother's milk by negative pressures.

BACKGROUND OF THE INVENTION

Generally, a breast pump for sucking out mother's milk includes a hood portion to be fitted on a breast, a pump for generating negative pressures in the hood portion and a milk reservoir for collecting the milk.

This kind of the breast pump is disclosed, for example, in an unexamined Japanese Patent Publication Hei 1-317448. In a conventional breast pump, a manually operatable pump is detached from the hood portion and reservoir and, then, is equipped to a driving unit. The piston of the pump is connected to an electrically powered piston driving means including a motor, or the like, which is equipped in a driving unit. The piston is reciprocated to generate negative pressures in the hood position for sucking mother's milk.

However, the above conventional breast pump is too large to carry because a driving unit is essential. Thus, it is desirable that a breast pump for sucking out mother's milk should be simple and easy to suck out mother's milk.

This invention is to solve the above problems, and its object is to provide a breast pump which is simple in structure and easy to suck out mother's milk easily.

SUMMARY OF THE INVENTION

The above object will be accomplished by the present invention. A breast pump for sucking out mother's milk according to the present invention includes a sucking portion to be fitted to one's breast, a negative pressure generating means mounted in the sucking portion for generating negative pressures therein, a driving means attached to the sucking portion, a driving power transmitting means attached to the sucking portion for repeatedly generating negative pressures by transmitting a driving power of the driving means and a reservoir connected to the sucking portion for reserving mother's milk from the sucking portion.

DETAILED DESCRIPTION OF THE PREFERRED EMBODIMENTS

Preferred embodiments of the present invention will now be described in detail, with reference to the accompanying drawings.

The following embodiments includes various preferable technical limitations because they are preferred concrete embodiments of the present invention. However, the scope of the present invention is not limited to them unless there is a description to so limit it.

Figure 1:
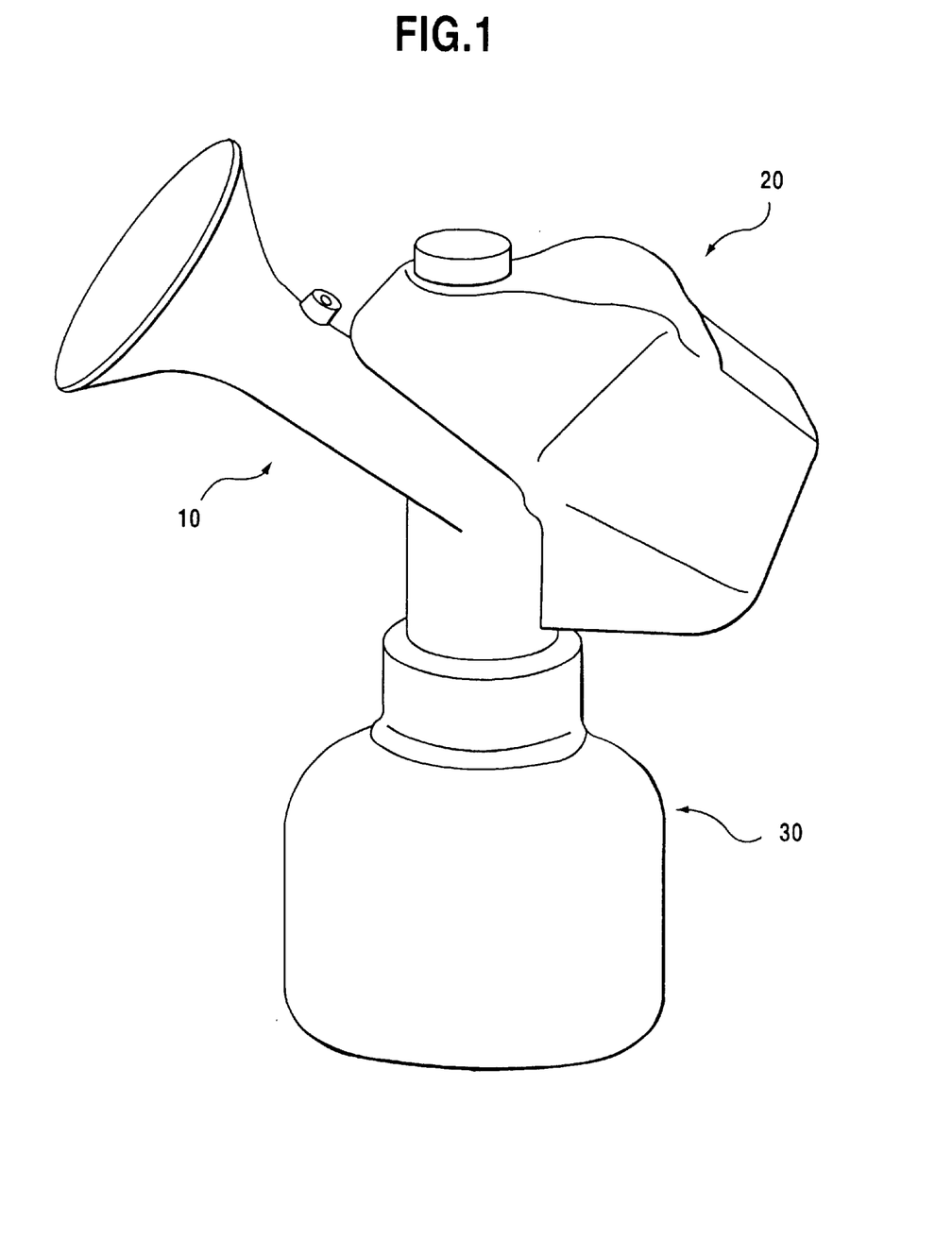
FIG. 1 is a perspective view of a breast pump according to the present invention.

FIG. 1 is a perspective view of a preferred embodiment of a breast pump according to the present invention. The breast pump shown in FIG. 1 includes a hood portion 10 for sucking mother's milk, a driving portion 20 for generating a driving power when mother's milk is sucked out and a reservoir 30 for collecting the sucked mother's milk. In the breast pump, the driving portion 20 is connected to the upper side of the hood portion 10 and the reservoir 30 is connected to the lower side of the hood portion 10.

Figure 2:
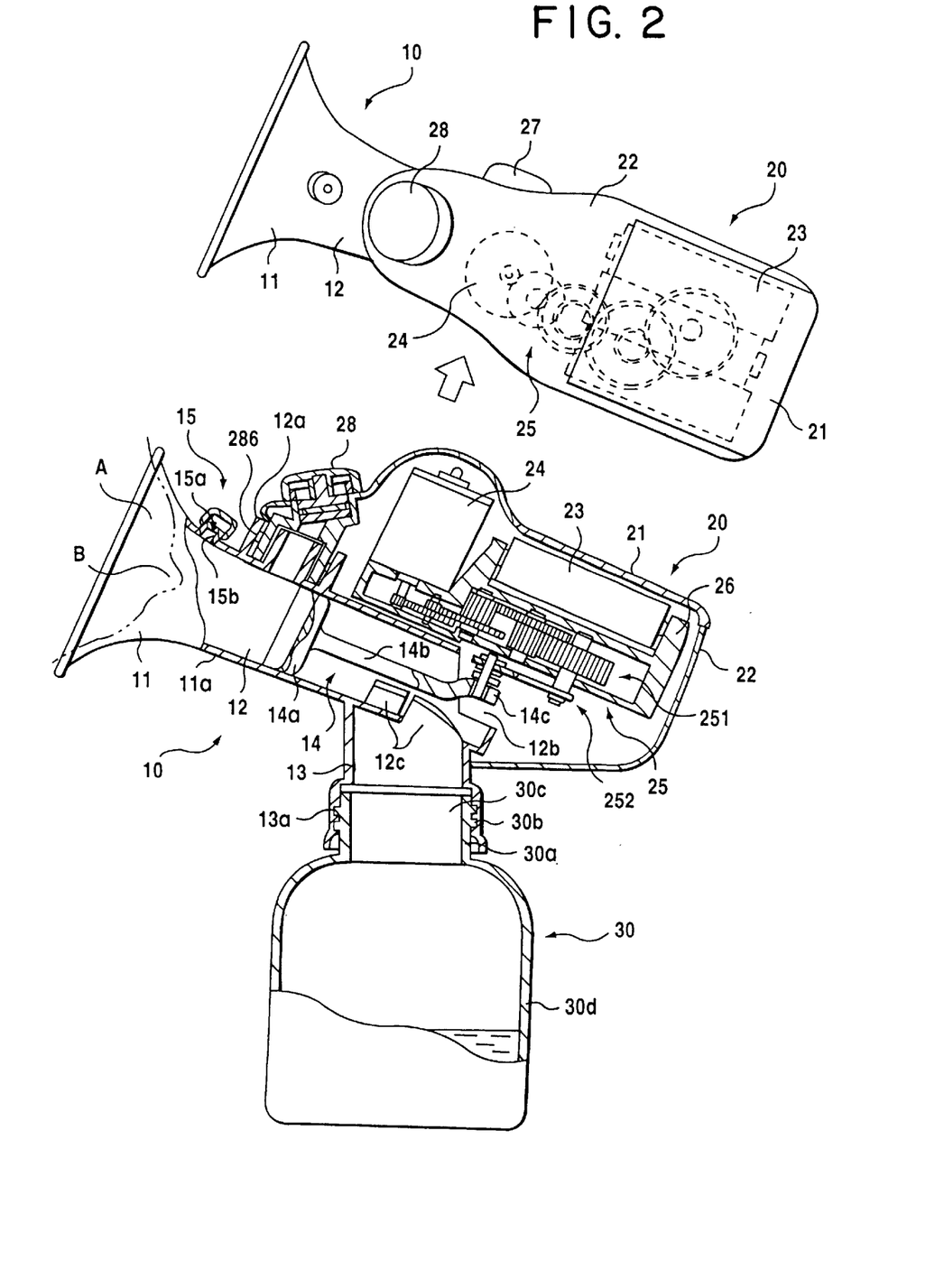
FIG. 2 is a plan view and a partial cross-sectional side view of the breast pump shown in FIG. 1.

The above embodiment will now be described in detail, with reference to FIG. 2 showing the top view and a partial cross-sectional view thereof.

The hood portion 10 is provided with a fitting portion 11, a cylindrical portion 12 integrally formed with the fitting portion 11 and a cap portion 13 integrally formed with the cylindrical portion 12. Further provided is a negative pressure generating means comprising a piston portion 14 which reciprocates in the cylindrical portion 12.

The fitting portion 11 has a configuration such that it fits one's breast A around the nipple B. The fitting portion 11 and the cylindrical portion 12 comprise a milk passage 11a.

Figure 3:
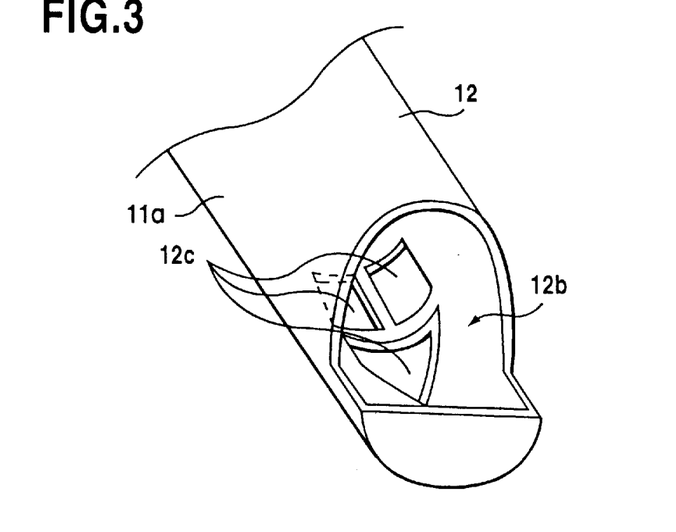
FIG. 3 is a perspective view of a cylindrical portion of the breast pump shown in FIG. 1.

Coaxial inner and outer cylindrical tubes 12a comprising a part of a pressure adjusting means 28 which will be described in detail later and a tube 15b having a valve 15a are integrally formed on the peripheral wall of the cylindrical portion 12. The cylindrical portion 12 has, at its end portion, a cutout portion 12b as shown in FIG. 3 so that an arm 14b of the piston portion 14 allows passing therethrough when the piston portion 14 reciprocates. At a connecting portion of the cylindrical portion 12 and the cap portion 13, a milk outlet 12c communicating with the milk passage 11a, for example, shown in FIG. 3, is provided.

A female screw thread 13a formed on the cap portion 13 is detachably engaged with a male screw thread 30b formed on a neck portion 30a of the reservoir 30.

Figure 4:
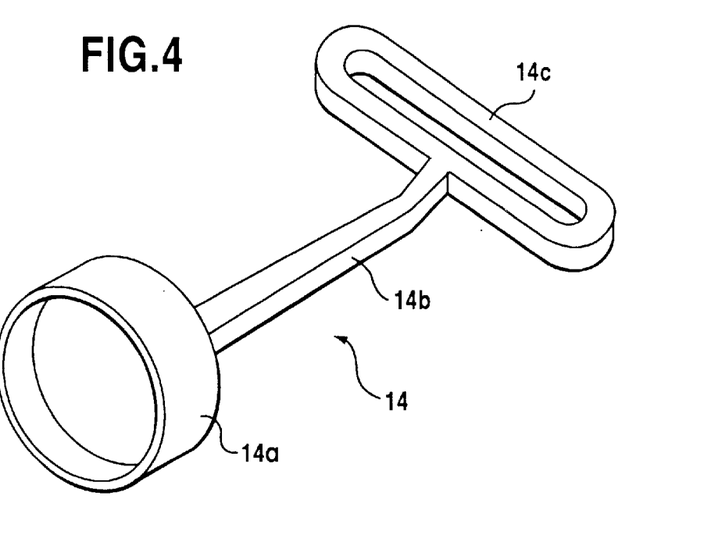
FIG. 4 is a perspective view of a piston portion of the breast pump shown in FIG. 1.

The piston portion 14 includes a cylindrical head portion 14a having a concave end portion which is slidably movable in an inner surface of the cylindrical portion 12, for example shown in FIG. 4, an arm 14b which is, at one end thereof, connected to the other end portion of the head portion 14a and an elongated ring-shaped guide 14c connected to the other end of the arm 14b. The head portion 14a is made of elastic materials, such as a silicone rubber, an isoprene rubber, a nitrile-butadiene rubber (NBR), or the like. The reason why the concave end portion is formed on the head portion 14a is to make a peripheral wall thin so as to facilitate its deformation, thereby enhancing smooth reciprocal movements of the head portion 14a in the cylindrical portion 12.

The fitting portion 11 of the hood portion 10, the cylindrical portion 12 and the cap portion 13 are preferably made of transparent materials, such as a polycarbonate (PC), polypropylene (PP), acrylic resin, acyrylonitrile-butadiene styren resin (ABS), or the like.

The driving portion 20 will be explained as follows.

The driving portion 20 has a first cover 21 and a second cover 22. The first cover 21 is detachably attached to the second cover 22. By removing the first cover 21 from the second cover 22, a power source 23 can be replaced. The first cover 21 and second cover 22 are preferably formed of transparent materials such as acyrylonitrile-butadiene styren resin (ABS), polypropylene (PP), a polycarbonate (PC), or the like, as mentioned above.

In the first cover 21 and second cover 22, there are a power source 23, such as a battery, a driving means 24, such as a DC motor connected to the power source 23, a driving power transmitting means 25, such as a gear connected to the driving means 24, a supporting base 26 for supporting the power source 23, the driving means 24 and the driving power transmitting means 25, a switch 27 disposed between the power source 23 and the driving means 24 and a pressure controlling means 28 for adjusting a pressure in the hood portion 10.

Three AA-size batteries for the power source 23 are detachably disposed in the supporting base 26. When an operator turns on the switch 27, a DC current is supplied to the driving means 24 from the power source 23. The power source 23 may be provided with an AC-DC adapter.

The driving power transmitting means 25 comprises a gear 251 for reducing a rotational power of the driving means 24 and a linkage 252 for converting rotational movements of the driving means 24 into reciprocating movements.

Figure 5:
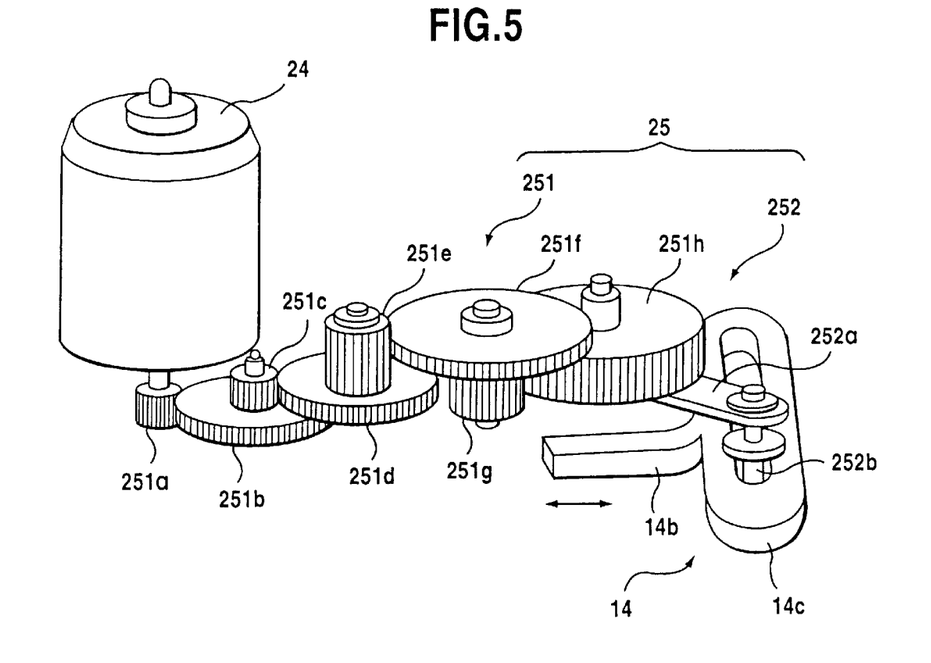
FIG. 5 is a perspective view of a driving means and driving power transmitting means of the breast pump shown in FIG. 1.

The gear 251 comprises reduction gears, for example, as shown in FIG. 5. The reduction gears includes a gear 251a fixed to an input axis of the driving means 24, a gear 251b engaged with the gear 251a, a gear 251c fixed to the axis of the gear 251b, a gear 251d engaged with the gear 251c, a gear 251e fixed to the axis of the gear 251d, a gear 251f engaged with the gear 251e, a gear 251g fixed to the axis of the gear 251f and a gear 251h engaged with the gear 251g. The reduction ratio of the gear 251 is, for example, 1/156.

The linkage 252 includes a crank 252a connected, at one end thereof, to an output axis of the gear 251h of the gear 251 and a slider 252b rotatably connected to the other end of the crank 252a. The slider 252b is inserted into the slot of the guide 14c of the piston portion 14.

Therefore, when an operator turns on the switch 27 to drive the driving means 24, the rotational driving power of the driving means 24 is transmitted to the crank 252a by way of the gears 251a, 251b, 251c, 251d, 251e, 251f, 251g, 251h. As a result, since the crank 252a rotates, the slider 252b connected to the other end of the crank 252a rotates with a radius equal to the length of the crank 252a. When the crank 252a rotates one time, the slider 252b reciprocates one time along the slot of the guide 14c of the piston portion 14 to push and draw the guide 14c. Thus, by continuously rotating the slider 252b, the guide 14c reciprocates within twice the length of the crank 252a in the direction perpendicular to the slot of the guide 14c (in the direction of the arrow shown in FIG. 5). The arm 14b and head portion 14a of the piston portion 14, which are integrally connected to the guide 14c, also reciprocate within twice the length of the crank 252a in the direction of the arrow shown in FIG. 5. Thus, the crank 252a, the slider 252b and the guide 14c form a mechanism for transforming rotational movements into reciprocating movements.

Figure 6:
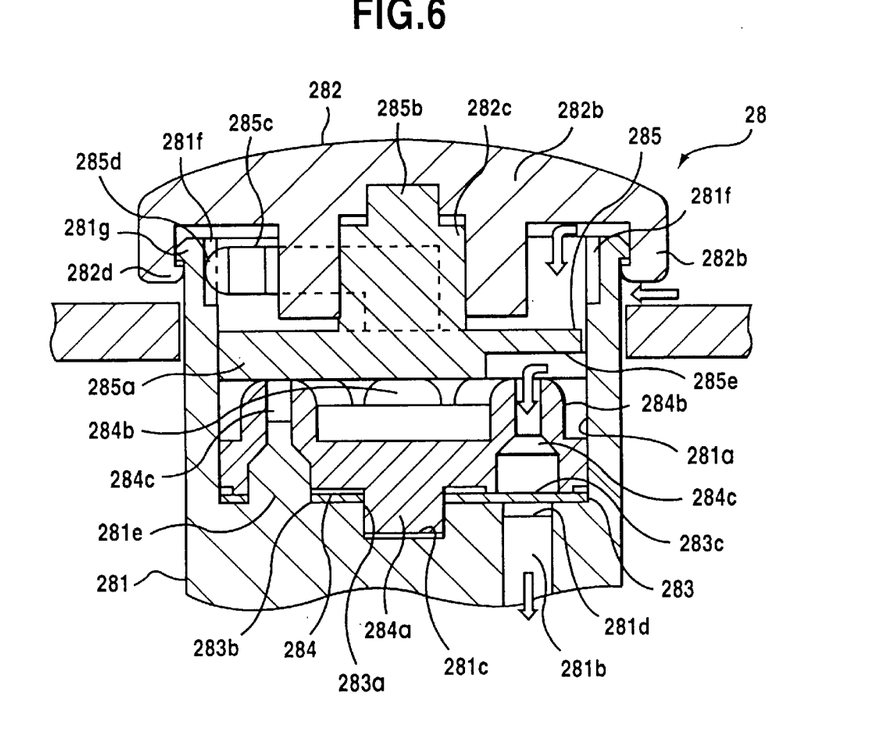
FIG. 6 is a perspective view of a pressure adjusting means of the breast pump shown in FIG. 1.
Figure 7:
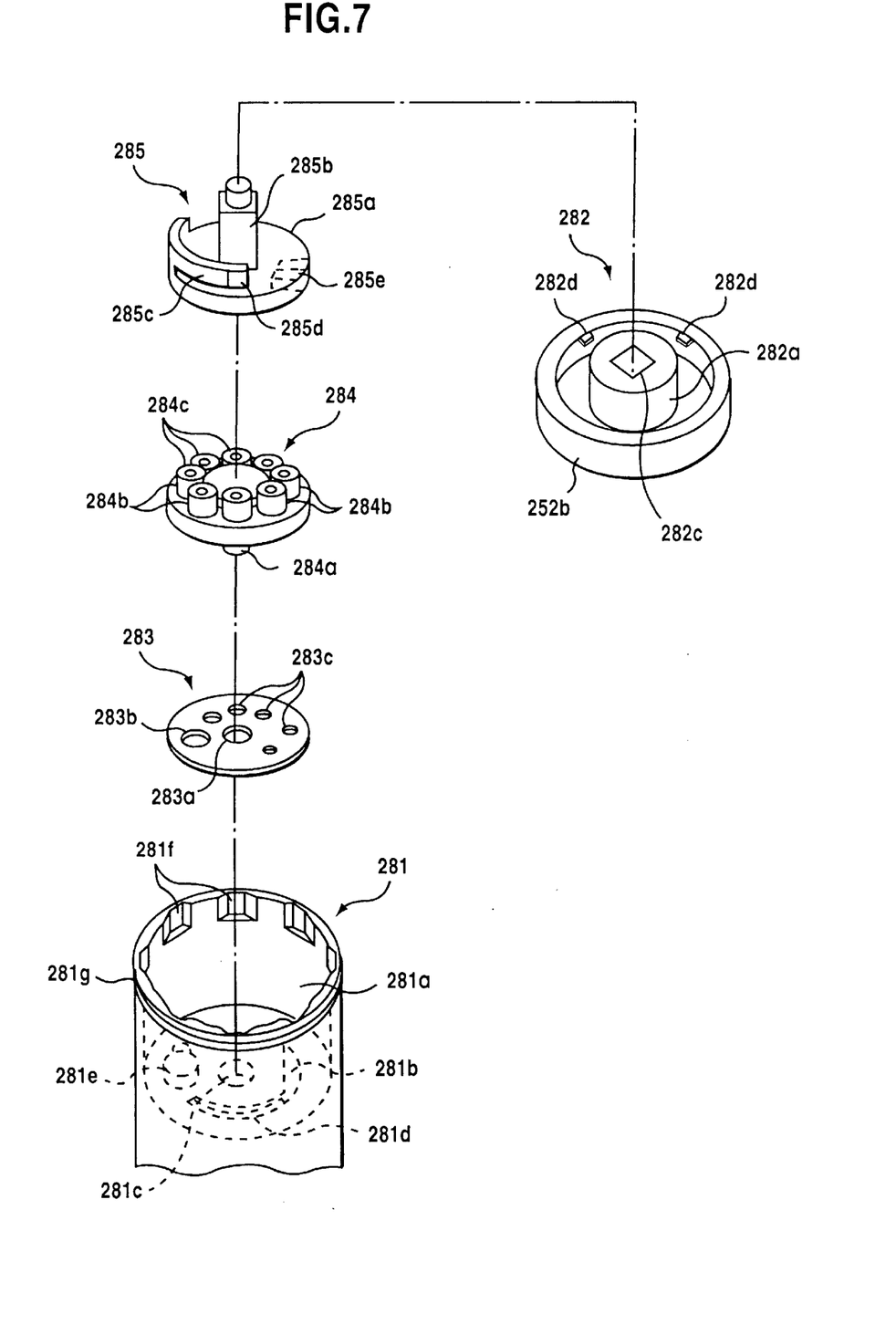
FIG. 7 is a perspective view of a pressure adjusting means, in a disassemble state, of the breast pump shown in FIG. 6.

The pressure adjusting means 28 includes an approximately cylindrical body 281 having a recessed portion 281a formed on one end thereof and a vent passage 281b formed in the recessed portion 281a, as shown in FIG. 6 showing the side sectional view and FIG. 7 showing the perspective view in a disassembled state. In the central portion of the bottom surface of the recessed portion 281a, a bearing hole 281c is formed. Outside of the bearing hole 281c, an arc-shaped communicating groove 281d communicating with the vent passage 281b and extending in the circumferential direction is formed. A positioning protrusion 281e is formed on the bottom surface of the recessed portion 281a apart from the end portion of the communicating groove 281d. Inside of the open end of the recessed portion 281a, a plurality of V-shaped cutout notches 281f are formed circumferentially equally spaced and a flange 281g for preventing a knob 282 from being pulled out is formed.

In the recessed portion 281a, a nozzle plate 283, a passage forming body 284 and a rotational part 285 are inserted one after another from the bottom of the dented portion 281a.

The nozzle plate 283 is a thin circular plate having a central hole 283a of the same size as the bearing hole 281c at the central portion thereof, a penetrated hole 283b for penetrating the positioning protrusion 281e outside of the central hole 283a and a plurality of nozzle holes 283c having different diameters each formed on the same radius so as to communicate with the communicating groove 281d.

The passage forming body 284 is a disc-shaped member. The body 284 has, at a central portion of one surface thereof, an axial protrusion 284a which is to be fitted in the bearing hole 281c through the central hole 283a. On the other surface of the body, protrusions 284b are formed at the corresponding portions of the penetrated holes 283b and nozzle holes 283c.

The protrusion 284b has a vent hole 284c which can be inserted onto the positioning protrusion 281e and prevents the passage forming body 284 from being rotated by the positioning protrusion 281e inserted into protrusion 284b. The opening ends of the vent holes 284c can be closed by the back surface of the rotational part 285.

The rotational part 285 includes a disc portion 285a loosely fitted in the recessed portion 281a, a rectangular column portion 285b protruding upwardly on the central portion of the disc portion 285a and an arm portion 285c protruding upwardly on the upper periphery of the disc portion 285a and having an arc-shaped upper portion. On the leading edge of the arm portion 285c, a notch protrusion 285d is outwardly protruded. On the bottom surface of the disc portion 285a, a fan-shaped cutout passage 285e, which can communicate with one of the plurality of vent holes 284c of the passage forming body 284, is formed.

The knob 282 has an inner cylindrical portion 282a and an outer cylindrical portion 282b which are concentric with each other. The inner cylindrical portion 282a has, at its central portion, a rectangular hole 282c for fitting the rectangular column portion 285b. By fitting the rectangular column portion 285b in the rectangular hole 282c, the rotational part 285 is integral with the knob 282 in the direction of the rotation. On the inner side of the outer cylindrical portion 282b, inwardly protruding portions 282d engaged with the flange 281g are formed to prevent the knob 282 from being pulled out from the body 281.

When the knob 282 is rotated, since the rotational part 285 is also rotated in the same direction, the cutout passage 285e formed on the back surface of the rotational part 285 is rotated in the same direction, thereby communicating with one of the vent hole 284c of the passage forming body 284. Each vent hole 284c of the passage forming body 284 is communicated with the vent passage 281b by way of one of the nozzle holes 283c, each being different in size and formed in the nozzle plate 283. Thus, a certain amount of outside air corresponding to the size of the nozzle hole 283c can flow into the vent passage 281b. Therefore, by selecting the nozzle hole 284c to adjust the amount of air flowing into the vent passage 281b, the negative pressure in the cylindrical portion 12 of the hood portion 10 can be adjusted.

When the knob 282 is rotated, since the notch protrusion 285d formed on the leading edge of the arm portion 285c of the rotational part 285 is moved from one of the notches 281f to the next, rotational resistance changes of the knob 282 are given and the notches 281f enable positioning of the rotational part 285.

The reservoir 30 includes a neck portion 30a having a male screw 30b engaged with the female screw 13a of the cap portion 13 as well as having an opening 30c and a container 30d for holding the mother's milk, which are integrally formed with the neck portion 30a. The container 30d has a relatively large bottom for stably standing the breast pump.

The reservoir 30 is preferably formed of transparent materials such as a polycarbonate (PC), a polypropylene (PP), a polyethylene, or the like.

By the way, the present invention is not limited to the above mentioned embodiment. For example, the power source 30, such as a battery, or the like, may be placed at the side of the reservoir 30 so that the stability of the breast pump can be enhanced. The driving means 24 is not limited to an electrically driven motor and may be a linear motor, a coil spring, or the like.

The operation of the above mentioned breast pump will be explained by using a flow chart and FIGS. 9–13 showing the operation. In the figures, the arrow MA denotes a flow of the mother's milk and the arrow AA denotes an air flow.

At first, the head portion 14a of the piston portion 14 is located at the position most adjacent to the fitting portion 11 of the hood portion 10, i.e., the top dead center and the valve 15a of the positive pressure opening means 15 is closed.

Figure 9:
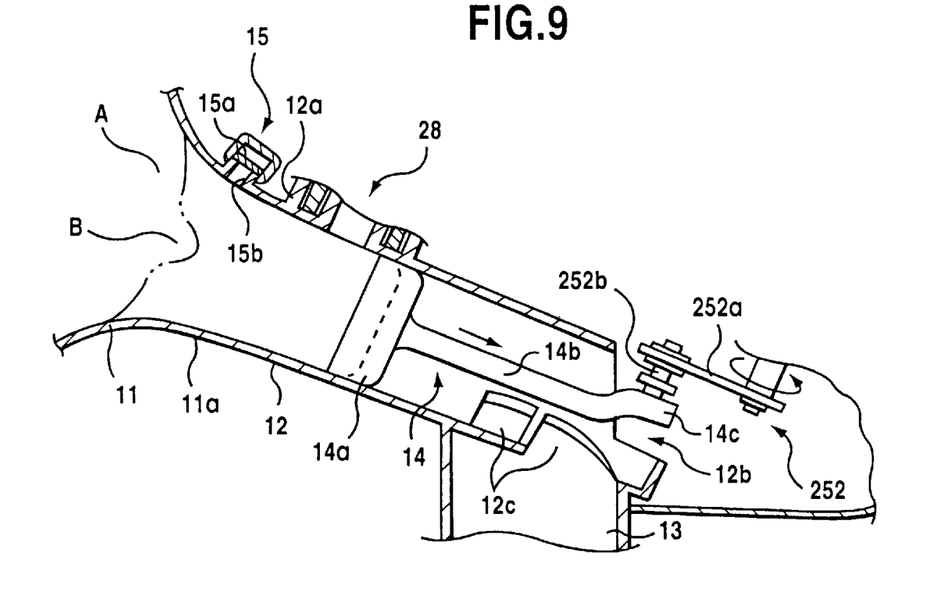
FIG. 9 is a first cross-sectional view showing an operation of the breast pump shown in FIG. 1.

As shown in FIG. 9, when an operator turns on the switch 27 with the fitting portion 11 fitted on one's breast (STP1), the power will be supplied from the power source 23 to the driving means 24 to rotate the gear 251 by the driving means 24 and the crank 252a of the linkage 252 rotates to slide the slider 252b in the guide 14c of the piston portion 14. Then, the arm 14b is drawn back by the the slider 252b and the head portion 14a starts to move from the top dead center toward the bottom dead center (STP2).

Figure 10:
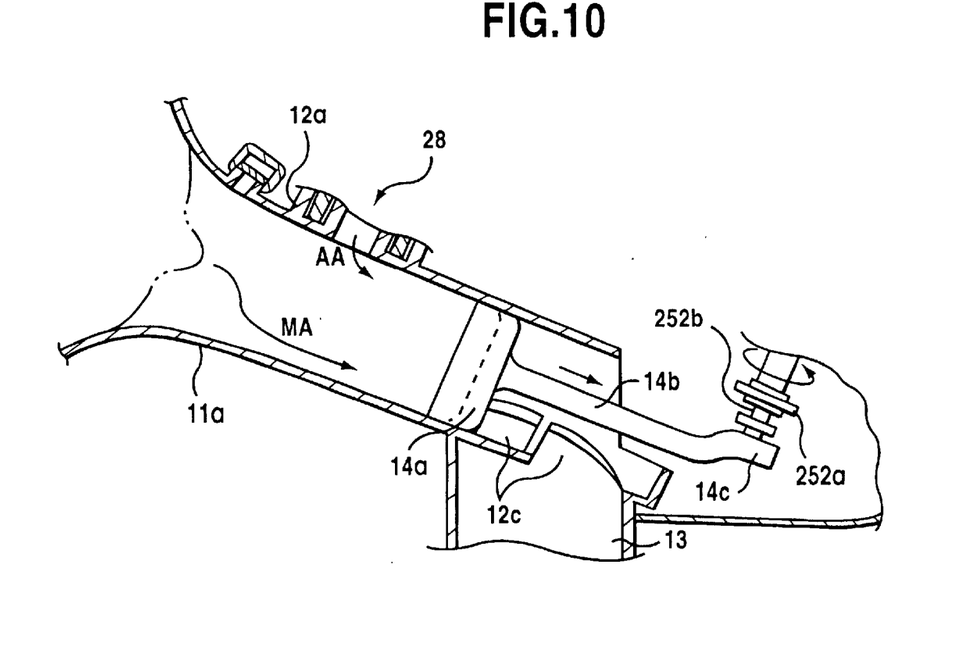
FIG. 10 is a second cross-sectional view showing an operation of the breast pump shown in FIG. 1.

As shown in FIG. 10, during the movement from the top dead center to the bottom dead center, a small amount of air is introduced through the pressure adjusting means 28 to cause a certain negative pressure in the cylindrical portion 12 (STP3) and sucking the mother's milk begins (STP4). The mother's milk flows toward the milk outlet 12c via the milk passage 11a (STP5).

Figure 11:
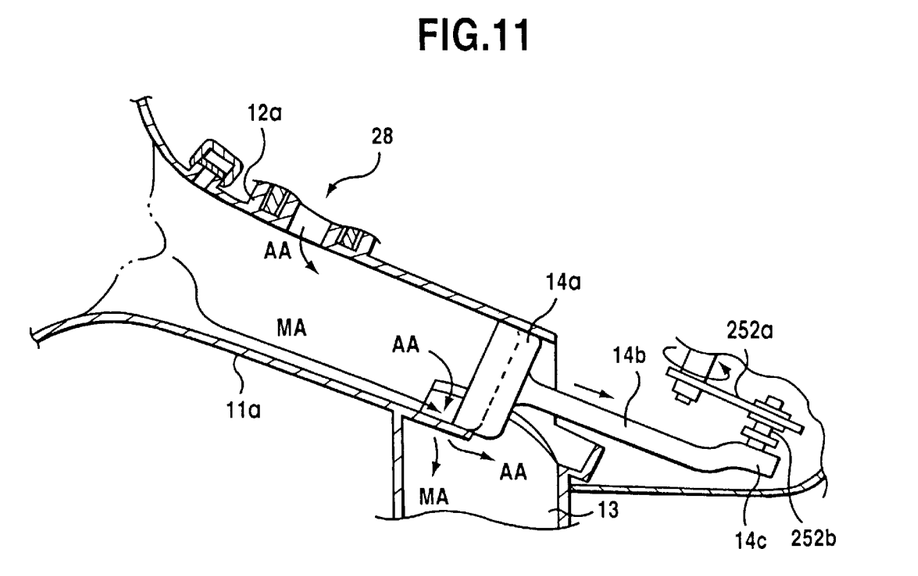
FIG. 11 is a third cross-sectional view showing an operation of the breast pump shown in FIG. 1.

As shown in FIG. 11, when the head portion 14a passes the milk outlet 12c, the mother's milk from the milk passage 11a flows down through the milk outlet 12c (STP6) and is collected in the container 30d (STP7). At the same time, air comes into the cylindrical portion 12 through the milk outlet 12c to release the negative pressure in the cylindrical portion 12. Thus, the pressure in the cylindrical portion 12 becomes an atomospheric pressure (STP7).

Figure 12:
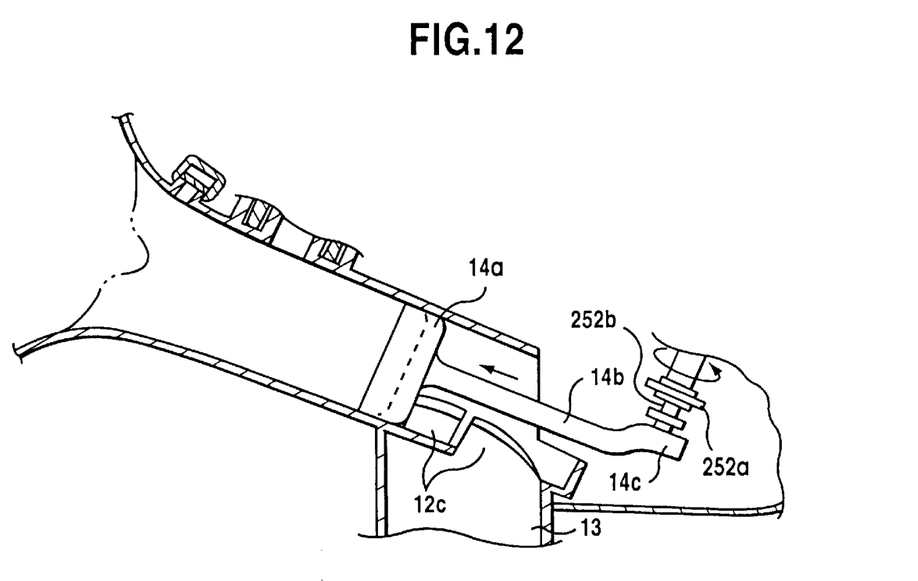
FIG. 12 is a forth cross-sectional view showing an operation of the breast pump shown in FIG. 1.
Figure 13:
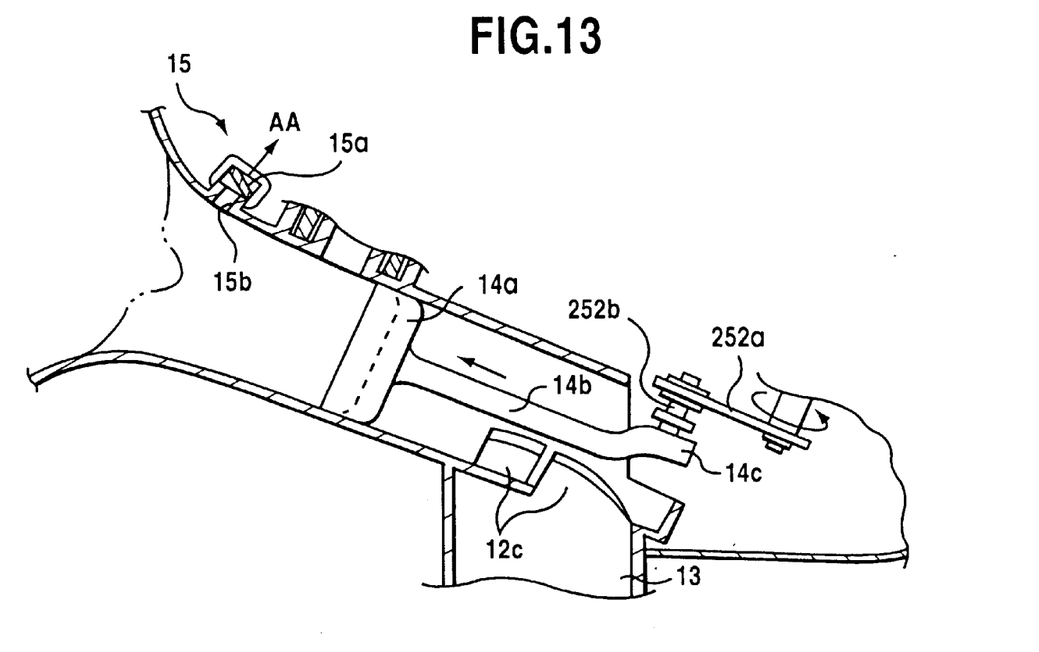
FIG. 13 is a fifth cross-sectional view showing an operation of the breast pump shown in FIG. 1.

As shown in FIG. 12, then, the arm 14 moves toward the top dead center as shown in FIG. 13, the pressure in the cylindrical portion 12 becomes a positive pressure. However, the valve of the positive pressure opening means 15 opens the opening thereof to allow the air to flow out of the cylindrical portion 12 through the opening of the positive pressure opening means 15. As a result, the positive pressure in the cylindrical portion 12 is released to become an atmospheric pressure (STP9).

Figure 8:
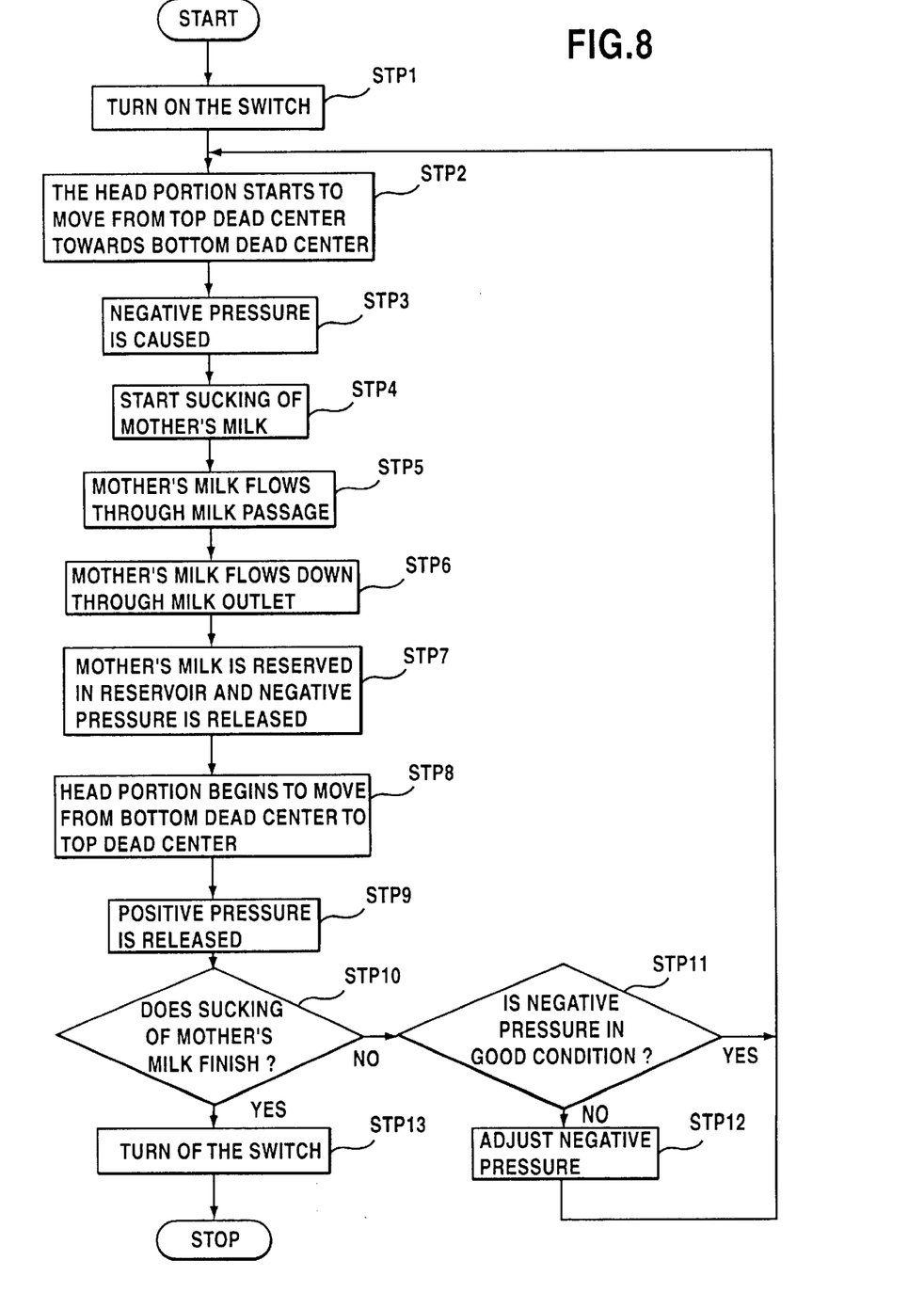
FIG. 8 is a flow chart showing an operation of the breast pump shown in FIG. 1.

The above mentioned operation comprises one cycle. When the operator wants to continue the sucking operation (STP10), the operator judges the sucking operation by the negative pressure (STP10). If the sucking operation is not in a good condition (STP11), the pressure adjusting means 28 is adjusted. If the sucking operation is in a good condition, the above operation from STP2 is repeated without adjusting the pressure adjusting means 28. When the operator wants to stop the sucking operation, the switch 27 is turned off (STP13).

In the operation mentioned above, an operator judges the sucking operation after one cycle is completed. However, the present invention is not limited to the above. In the actual sucking operation, the operator may want to judge the sucking operation for a while. In such a case, the operator may judge the sucking operation by the negative pressure and may adjust the pressure adjusting means 28 during the operation.

Figure 14:
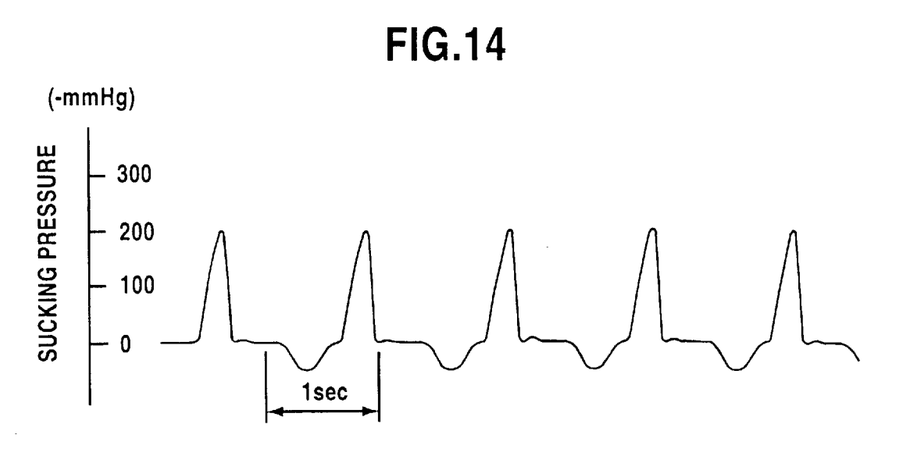
FIG. 14 is an example of a graph showing the sucking pressure of the breast pump shown in FIG. 1.
Figure 15:
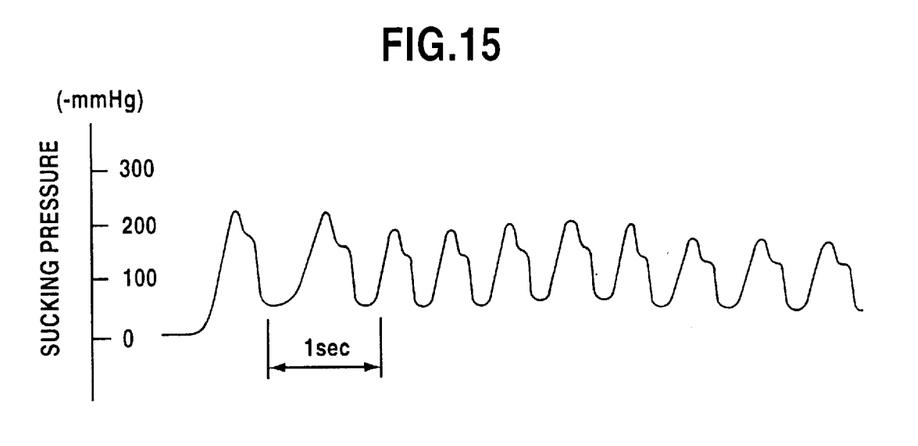
FIG. 15 is an example of a graph showing the sucking pressure of a baby.

FIG. 14 shows an example of the sucking pressure curve of the breast pump according to the present invention. FIG. 15 shows an example of the sucking pressure curve of an infant.

Figure 16:
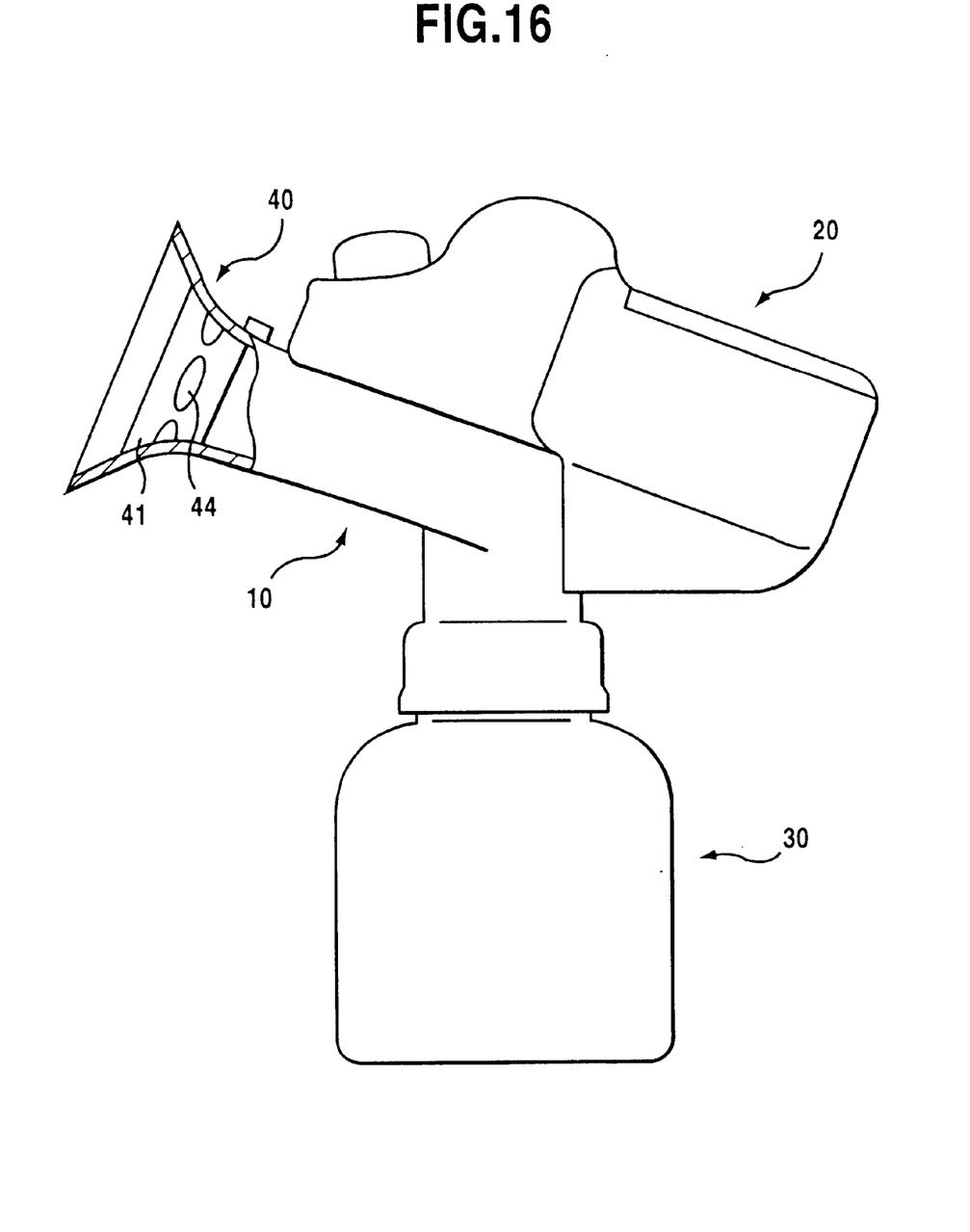
FIG. 16 is a side view of another embodiment having a nipple adapter according to the present invention.

The sucking pressure curve of the breast pump according to the present invention shows the similar pulsation of the sucking pressure curve of an infant. In the breast pump according to the present invention, the sucking pressure may preferably be set above the actual sucking pressure of an infant. The reason is as follows. In actuality, it is believed that a nipple adapter 40 may be added to the embodiment shown in FIG. 1. The nipple adapter 40 is used for preventing pain in the breast A caused by sucking during the sucking operation by the hood portion 10.

Figure 17:
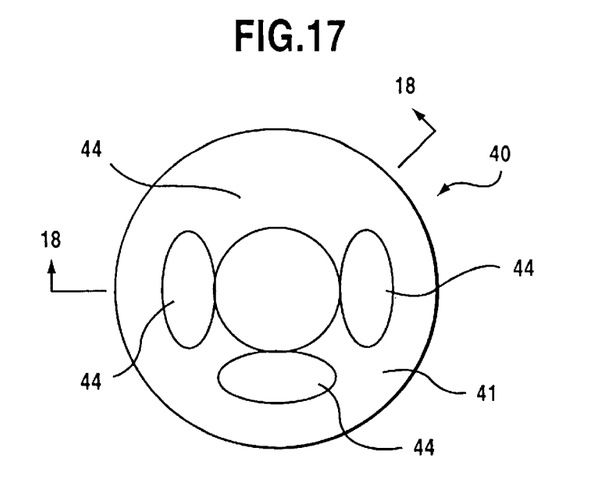
FIG. 17 is a front view of the nipple adapter.
Figure 18:
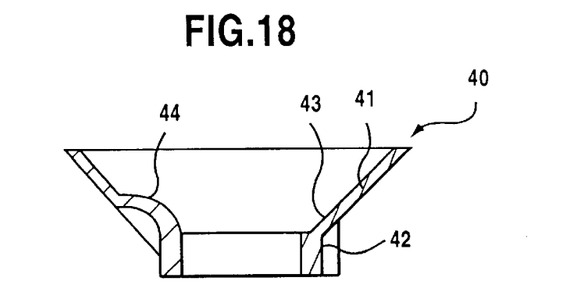
FIG. 18 is a cross-sectional view of the nipple adapter taken along the line A—A in FIG. 17.
Figure 19:
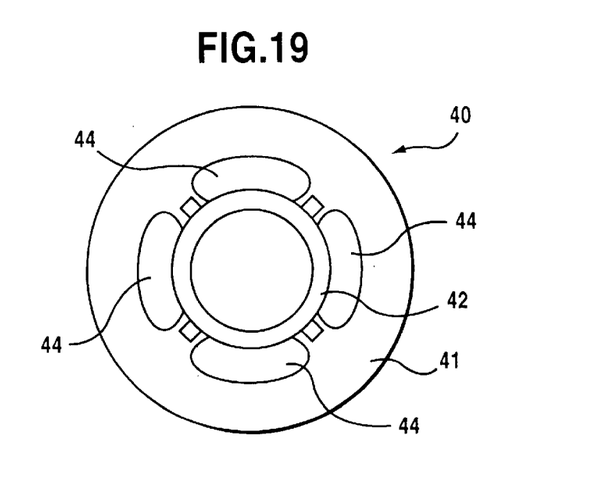
FIG. 19 is a rear view of the nipple adapter.

As shown in FIGS. 17–19, the nipple adapter 40 comprises a receiving portion 41 and a portion 42. The receiving portion 41 is formed conical, and the small diameter portion 43 of the receiving portion 41 is connected to the portion 42. The portion 42 is formed to be a cylinder and has a passage for the mother's milk. The nipple adapter 40 is positioned by contacting the receiving portion 41 and the portion 42 to the inner surface of the hood portion 10.

The receiving portion 41 is provided with a plurality of bulged portions 44. By sucking operation by the hood portion 10, one's breast is pressed by these bulged portions 44 and thus massage effects, like stimulating or pressing by the finger, are obtained. Thus, by the synergistic effect of the function of the nipple adapter 40 and the pulsation sucking operation mentioned above, the sucking operation can become similar to the real stimulation or massage by fingers, or become similar to the sucking operation by an infant.

Figure 20:
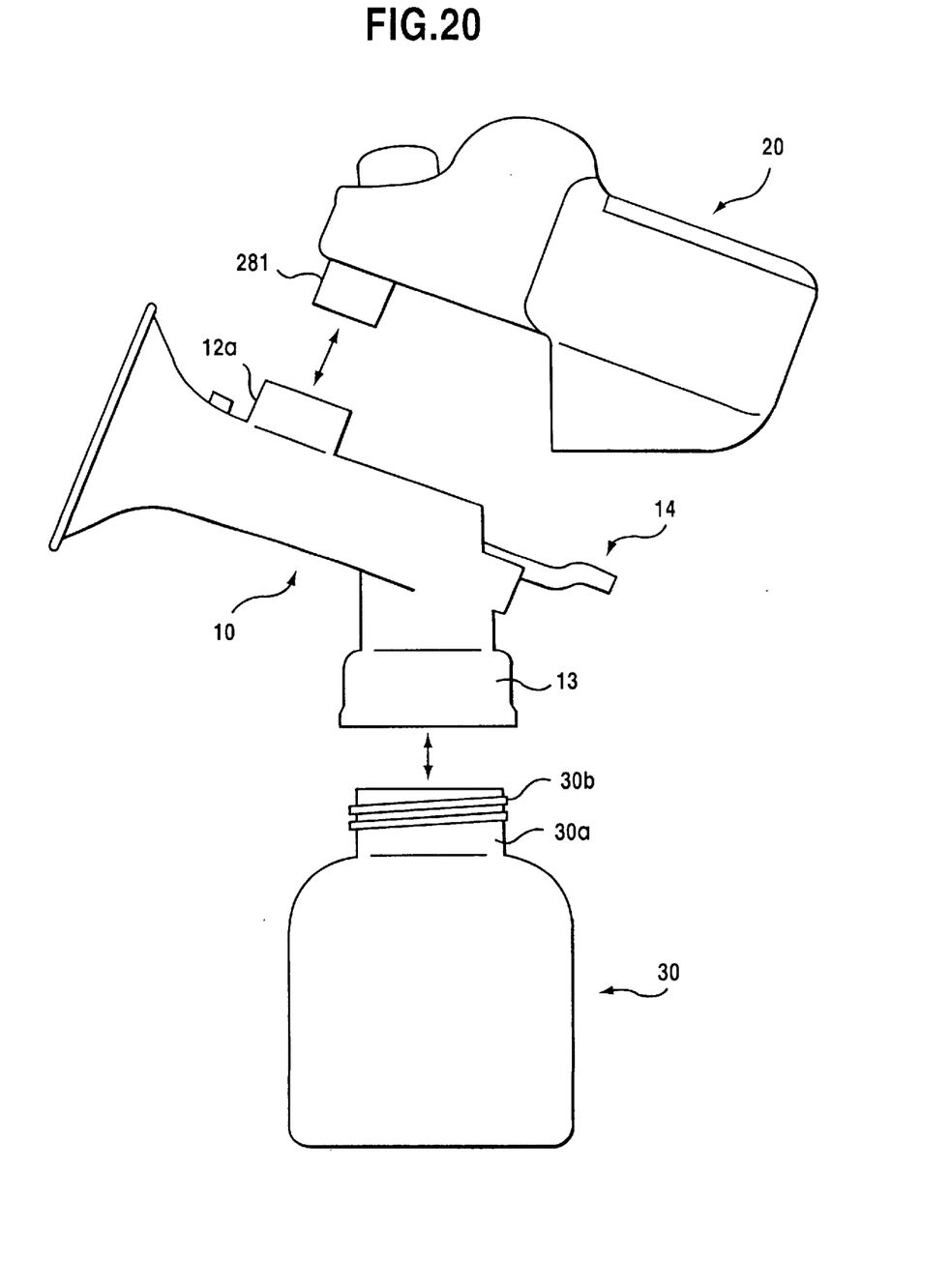
FIG. 20 is a perspective view of the breast pump in a disassembled state shown in FIG. 1.

Before or after using the breast pump mentioned above, the breast pump should be sterilized by boiling. Thus, the hood portion 10 of the breast pump, the driving portion 20 and the reservoir 30 can be disassembled as shown in FIG. 20. The driving portion 20 mounted on the upper portion of the hood portion 10 can be pulled off from the driving portion 20 because the tube 12a formed on the cylindrical portion 12 and the body 281 of the pressure adjusting means 28 are connected by way of an O-ring 286. The reservoir 30 disposed under the hood portion 10 can be detached from the hood portion 10 by rotating the reservoir 30 while holding the hood portion 10 because the reservoir 30 is connected to the hood portion 10 by engaging the female screw 13a of the cap portion 13 with the male screw 30b of the neck portion 30a. If the driving portion 20 is made to be waterproof, it will be possible to integrally form the hood portion 10 and the driving portion 20 because the driving portion 20 can be sterilized by boiling.

Figure 21:
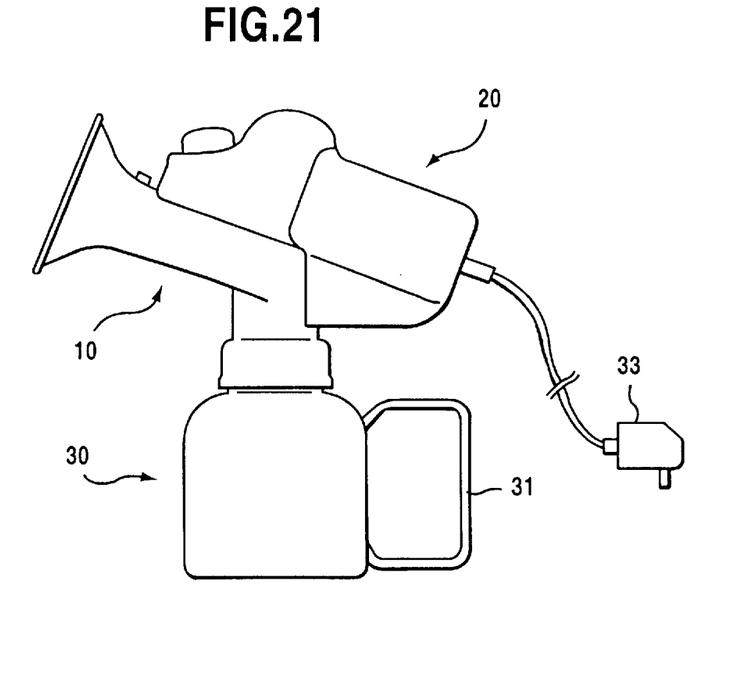
FIG. 21 is a side view of another embodiment of a breast pump according to the present invention.
Figure 22:
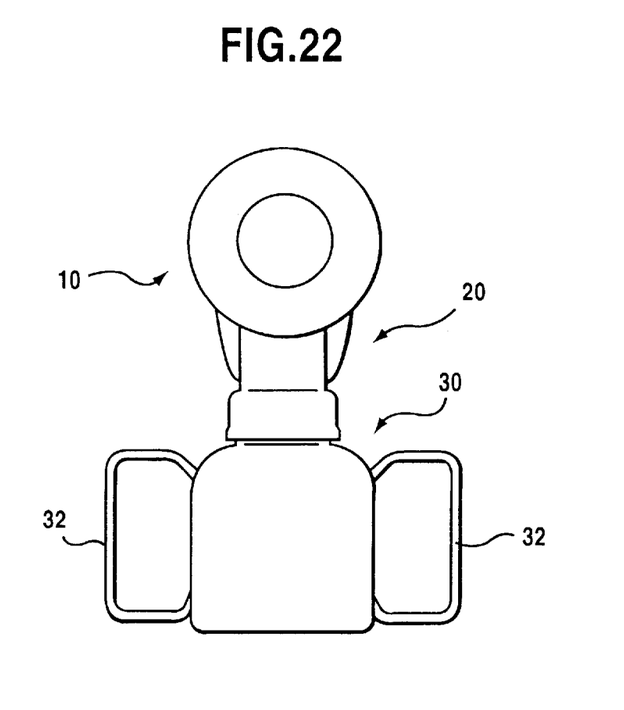
FIG. 22 is a plan view of still another embodiment of a breast pump according to the present invention.

As shown in FIGS. 21 and 22, a handle 31 may be added to the reservoir 30 at the opposite side to the hood portion 10 or a pair of handles 32 may be added to the reservoir 30 at both side to the hood potion 10 so as to enhance easy operation and stability of the breast pump.

As shown in FIG. 21, an AC adapter 33 may be connected to the driving portion 20 to supply the power. The AC adapter 33 transforms, for example, a commercial AC 100 volt into DC 4.5 volt. When the AC adapter 33 is used, the battery may be attached or detached. The AC adapter 33 can be connected to the breast pump shown in FIG. 1 and FIG. 23.

As described above, according to the present invention, the breast pump can be simple in structure and can easily suck out the mother's milk.

INDUSTRIAL APPLICABILITY

As mentioned above, the present invention is suitably used to suck out the mother's milk by negative pressures.

What is claimed is:

1. A breast pump for sucking out mother's milk comprising;
    a hood portion containing a fitting portion to be fitted to a breast;
    a reservoir for receiving mother's milk obtained from said breast;
    means for generating negative pressures in said hood portion including means forming a milk passage extending from said hood portion and attaching to said reservoir, a piston slidably movable in said milk passage, driving power transmitting means including a crank drivingly connecting said piston, and electrically powered driving means operatively connected to said crank for driving said piston; and
    means for adjusting negative pressures in said hood portion including an air intake opening mounted on said milk passage forming means at a location upstream of said piston, and means for selectively adjusting the size of said opening for adjustably regulating the negative pressures generated in said hood portion.

2. The breast pump as recited in claim 1, further comprising a positive pressure releasing means mounted on said hood portion upstream of said negative pressure adjusting means for releasing a positive pressure generated in said hood portion.

3. The breast pump as recited in claim 1, wherein said driving means is a DC motor.

4. The breast pump as recited in claim 1, wherein said driving means is driven by a battery.

5. The breast pump as recited in claim 1 wherein said piston is driven by way of an AC adapter.

6. The breast pump as recited in claim 1 wherein said driving power transmitting means includes a linkage for transforming rotational motions of said driving means into reciprocating motions of said piston.

7. The breast pump as recited in claim 1 wherein said driving power transmitting means includes gears for reducing the output generated by said driving means.

8. The breast pump as recited in claim 1 wherein said hood portion, said negative pressure generating means and said driving power transmitting means are detachably connected to said reservoir.

* * * * *